(12) United States Patent
Barnes et al.

(10) Patent No.: US 8,454,544 B2
(45) Date of Patent: Jun. 4, 2013

(54) METHOD AND APPARATUS FOR THERAPEUTICALLY SUPPORTING THE ARM OF A PATIENT

(76) Inventors: William S. Barnes, Forsyth, GA (US); Christopher C. Bidwell, Dunwoody, GA (US); George W. Stough, Alpharetta, GA (US)

( * ) Notice: Subject to any disclaimer, the term of this patent is extended or adjusted under 35 U.S.C. 154(b) by 211 days.

(21) Appl. No.: 12/715,172

(22) Filed: Mar. 1, 2010

(65) Prior Publication Data

US 2011/0005525 A1    Jan. 13, 2011

Related U.S. Application Data

(60) Provisional application No. 61/208,744, filed on Feb. 27, 2009.

(51) Int. Cl.
*A61F 5/00* (2006.01)

(52) U.S. Cl.
USPC .................... 602/4; 602/19; 602/20

(58) Field of Classification Search
USPC .... 602/4, 5, 19–22; 128/876, 878; 2/336–338
See application file for complete search history.

(56) References Cited

U.S. PATENT DOCUMENTS

| | | | | | |
|---|---|---|---|---|---|
| 4,751,923 | A | * | 6/1988 | Marino | 602/4 |
| 5,178,163 | A | * | 1/1993 | Yewer, Jr. | 128/876 |
| 5,558,626 | A | * | 9/1996 | Holtzman et al. | 602/4 |
| 6,666,838 | B2 | * | 12/2003 | Modglin et al. | 602/19 |
| 2005/0273026 | A1 | * | 12/2005 | Howard | 602/20 |
| 2007/0054758 | A1 | * | 3/2007 | Cockrell | 473/458 |

\* cited by examiner

*Primary Examiner* — Michael A. Brown

(57) ABSTRACT

Apparatus for providing physical therapy to a patient, the apparatus comprising a therapeutic support comprising a waist belt and a limb support, wherein the limb support is adjustably securable to the waist belt.

17 Claims, 21 Drawing Sheets

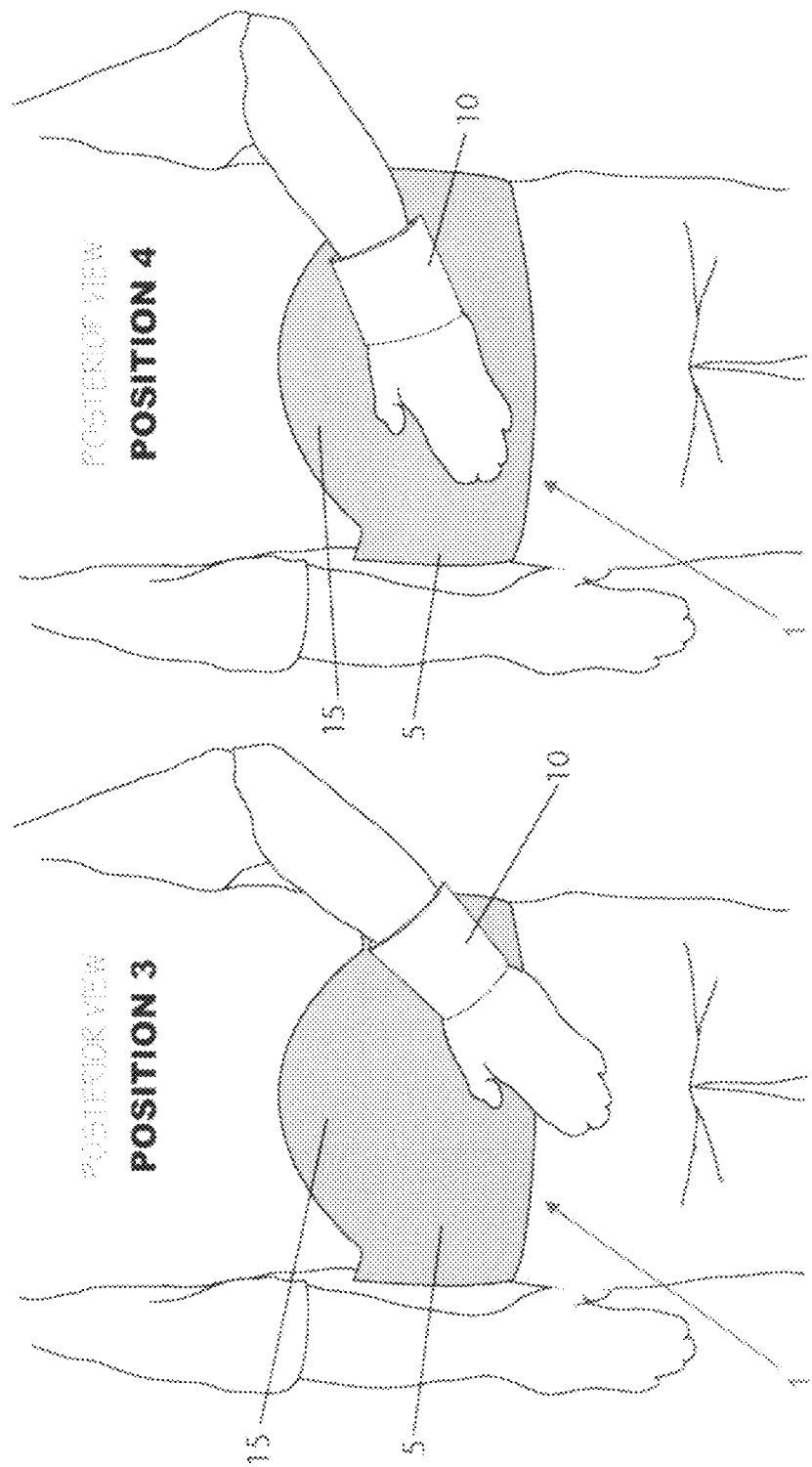

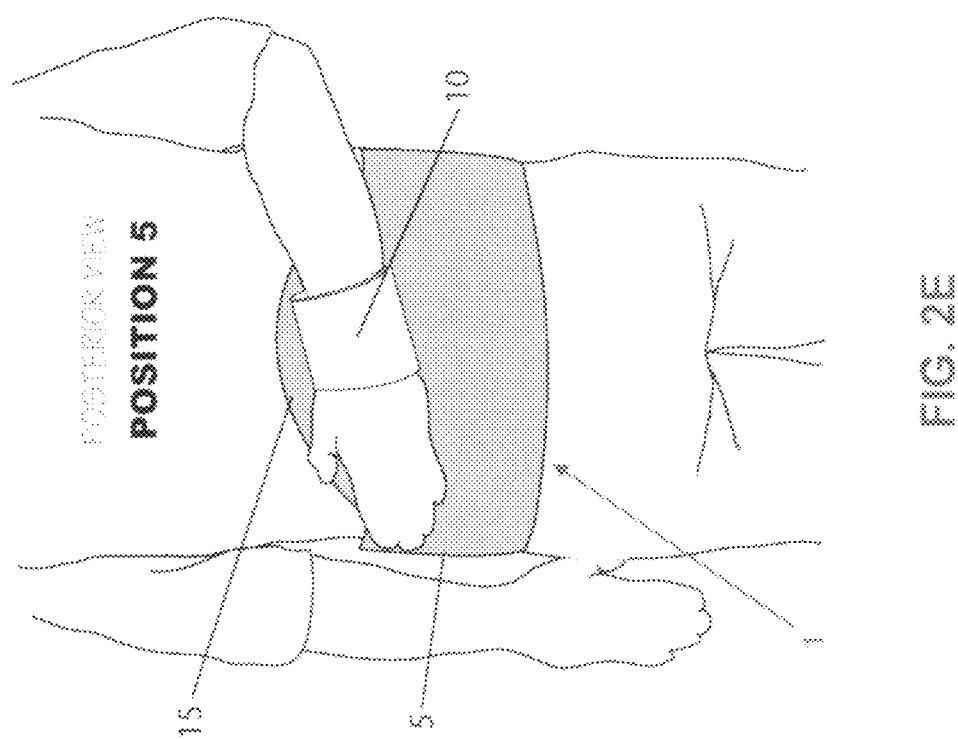

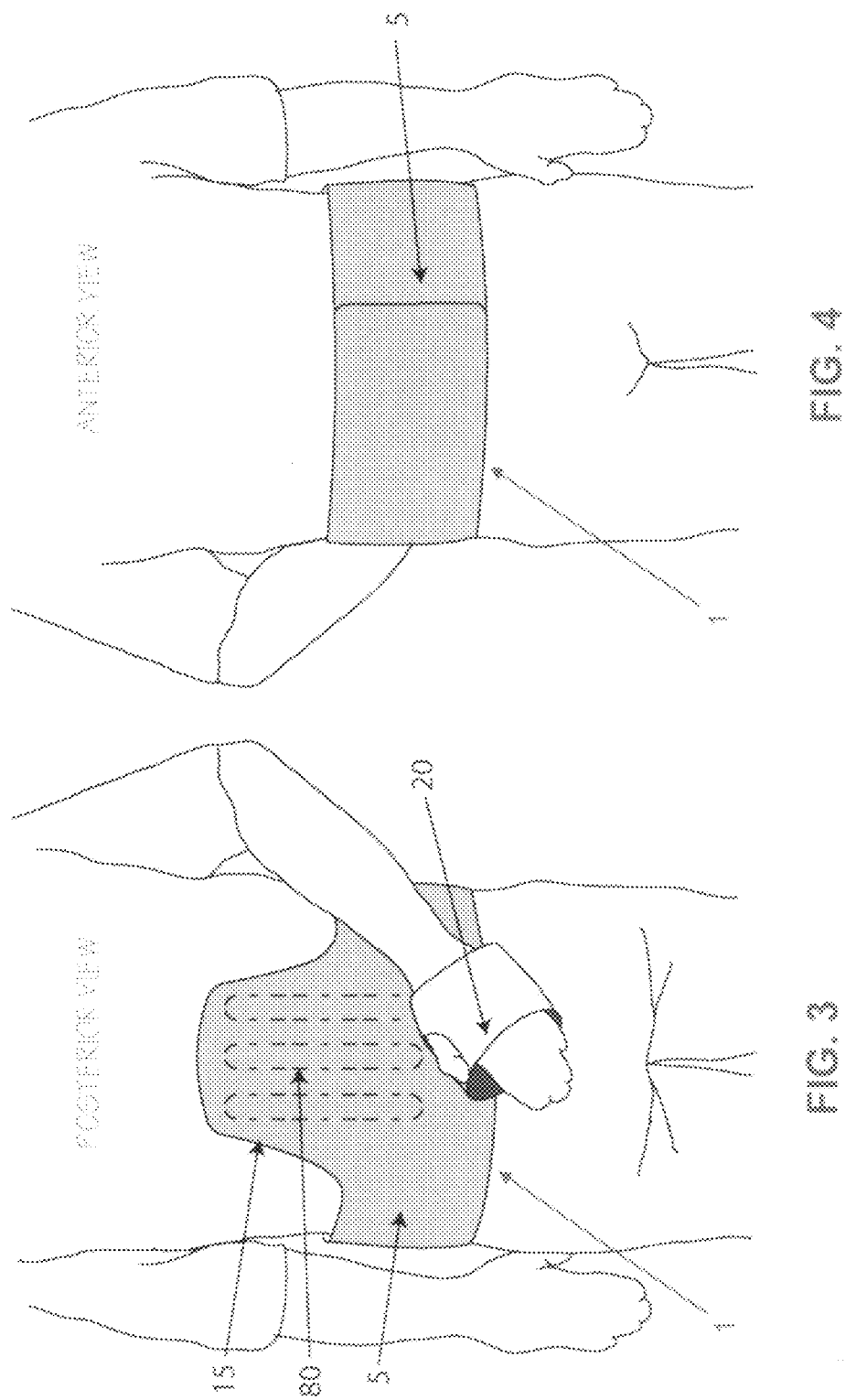

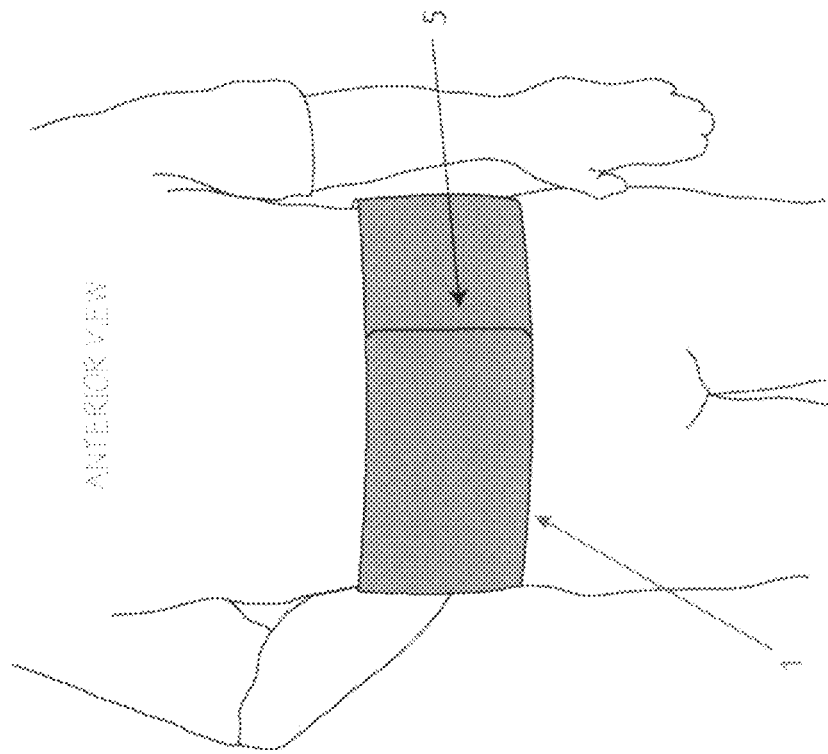
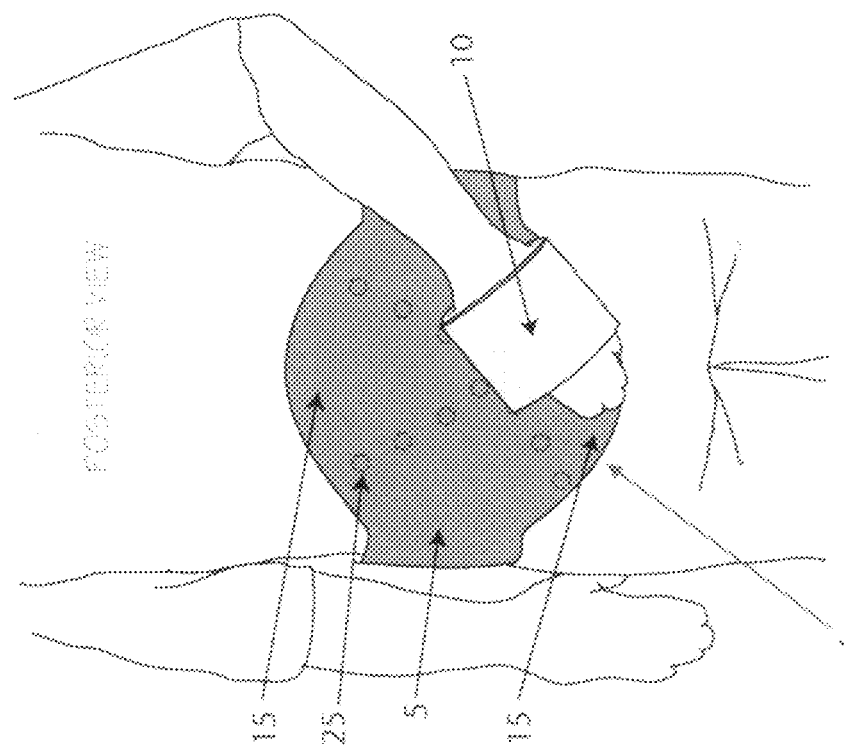

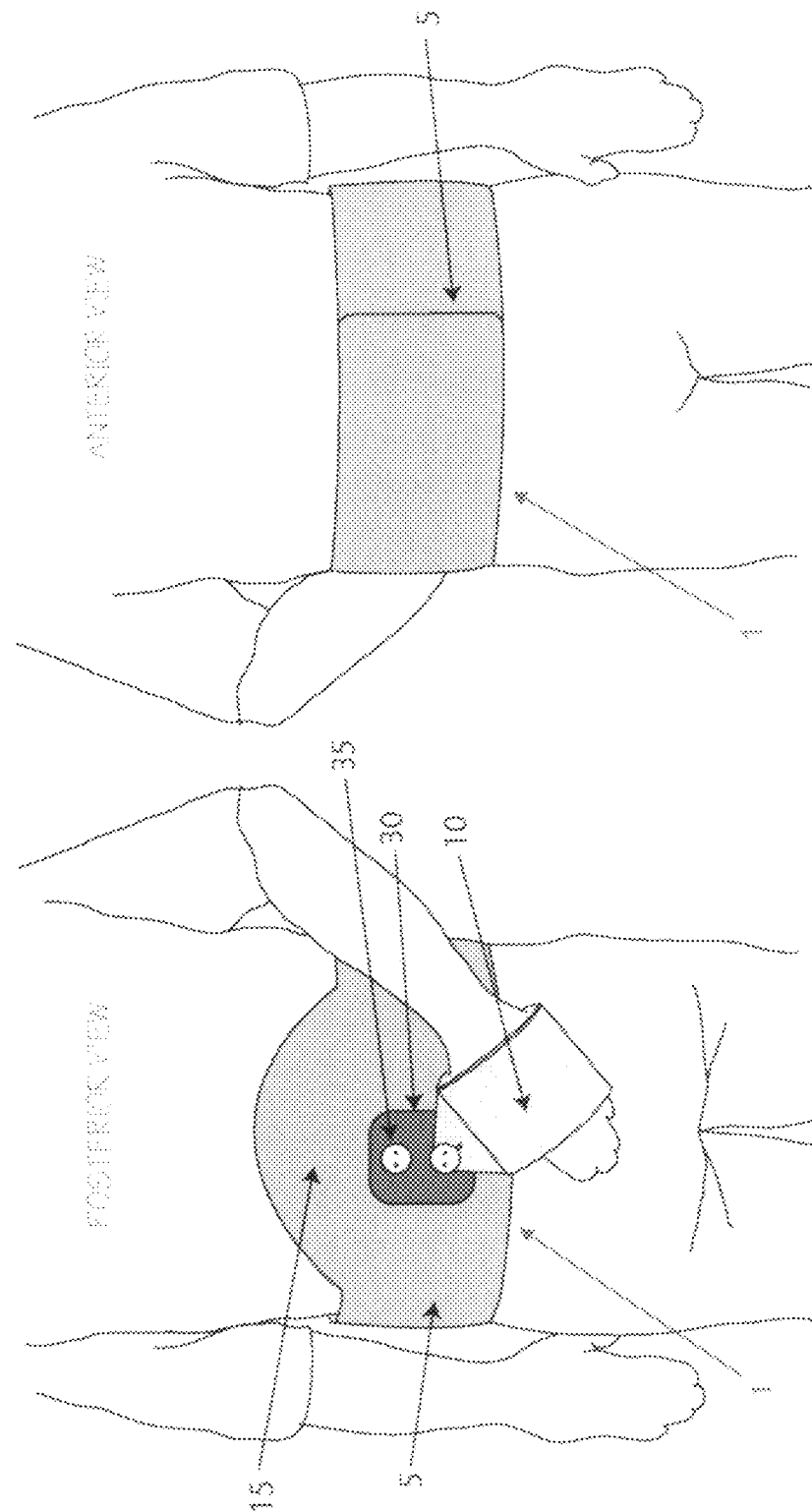

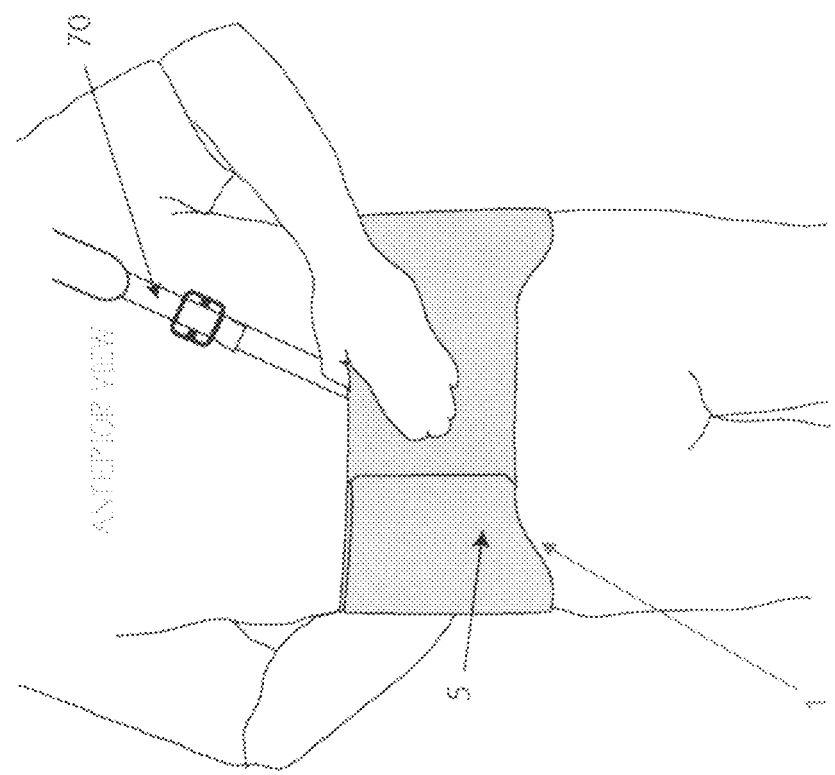
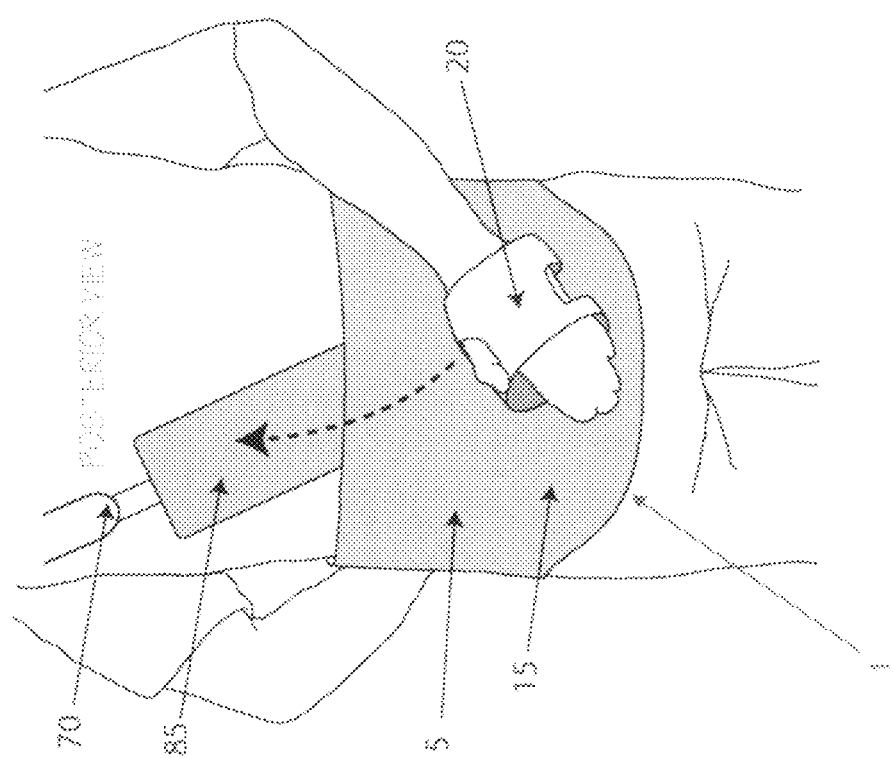
FIG. 14
FIG. 13

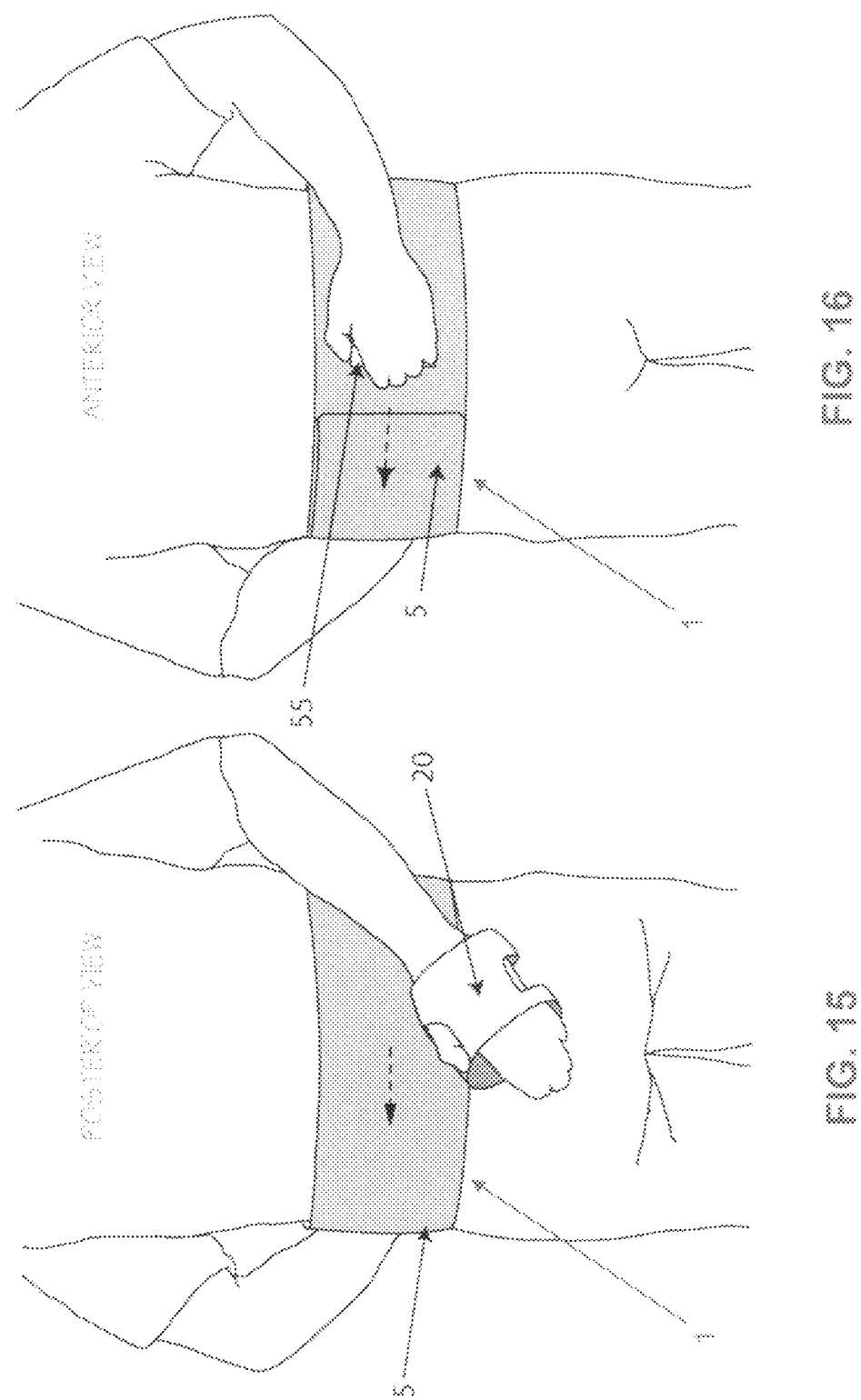

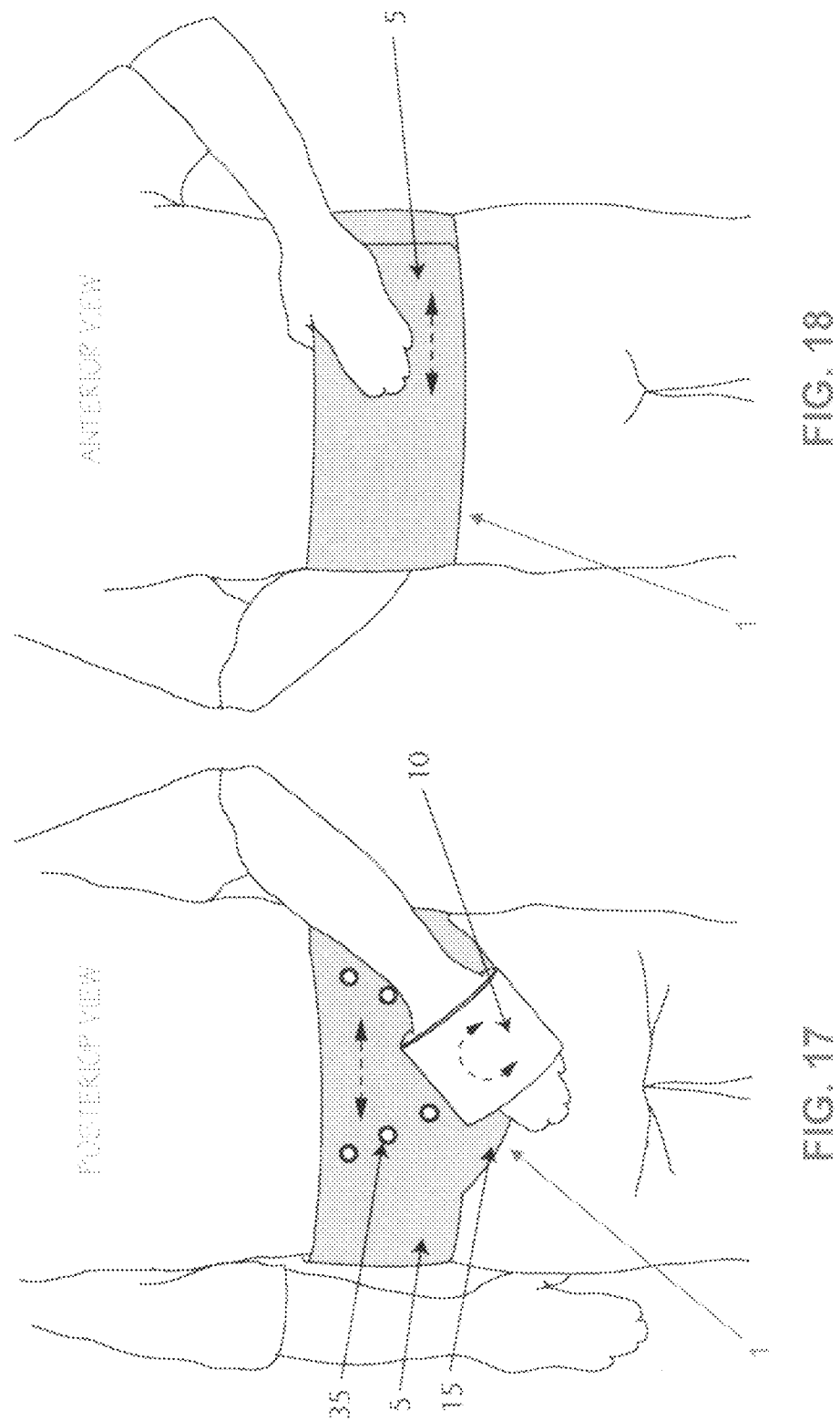

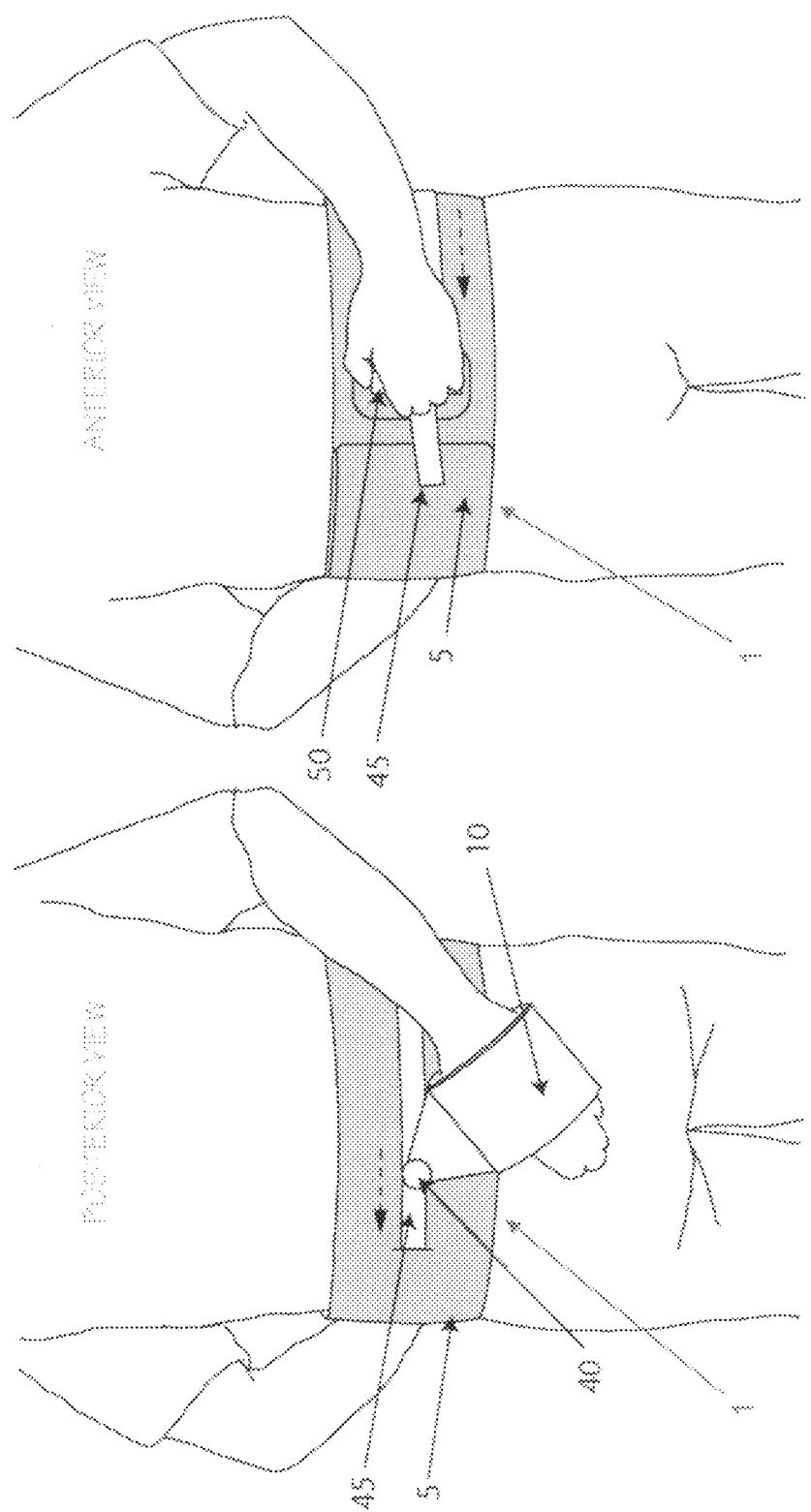

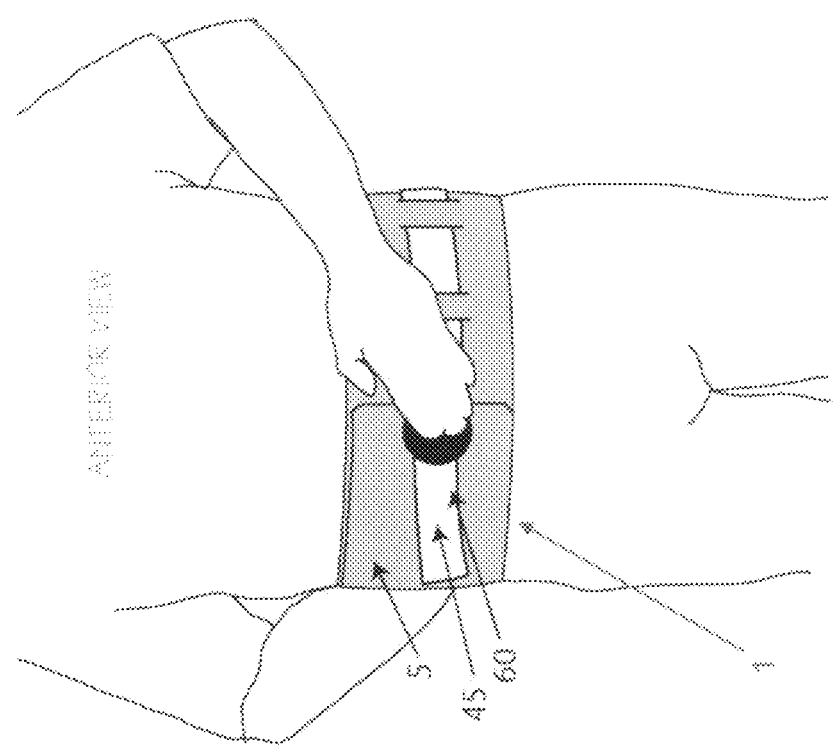
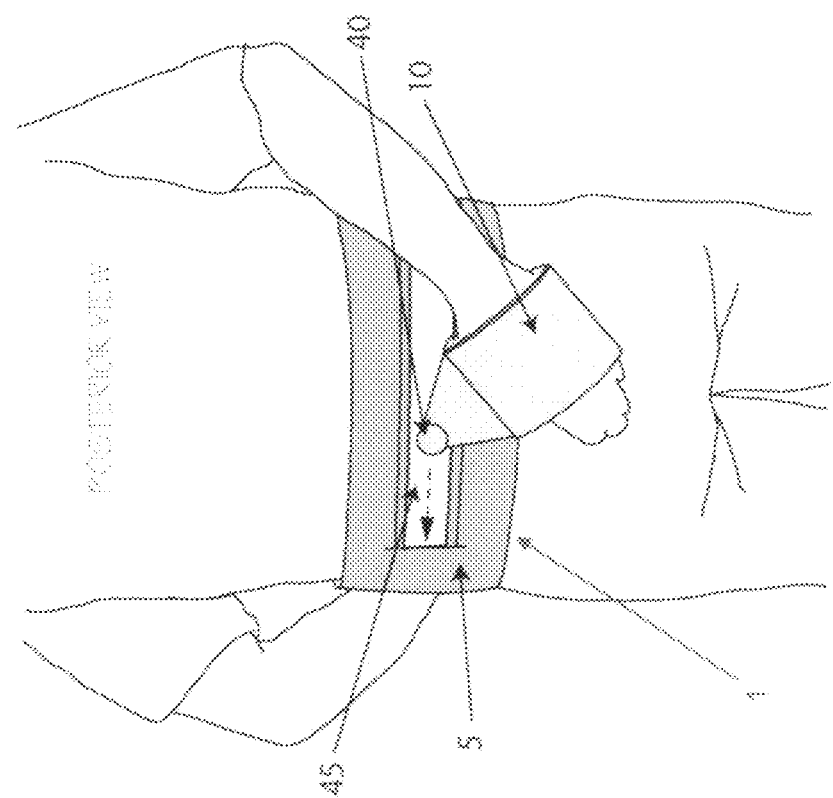

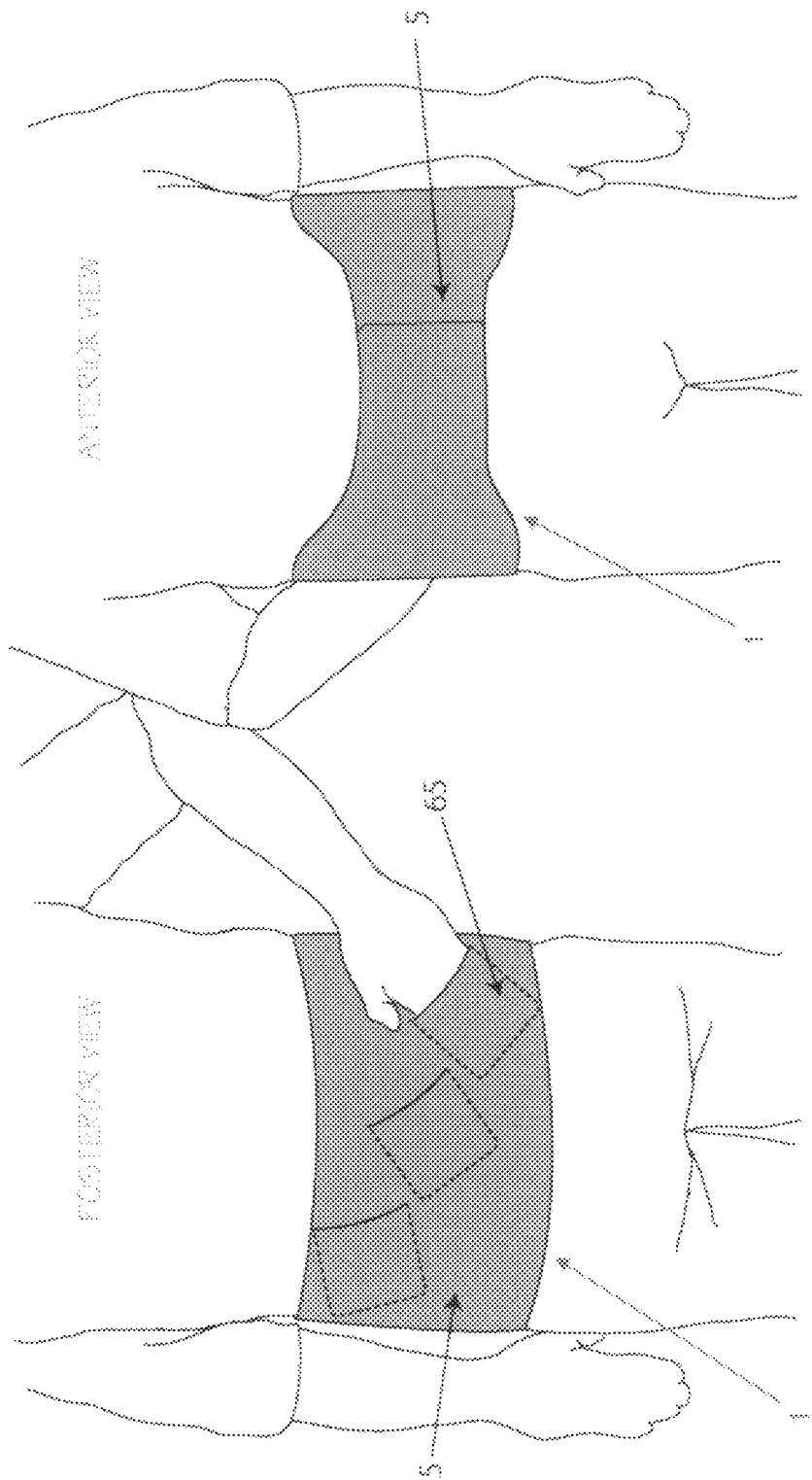

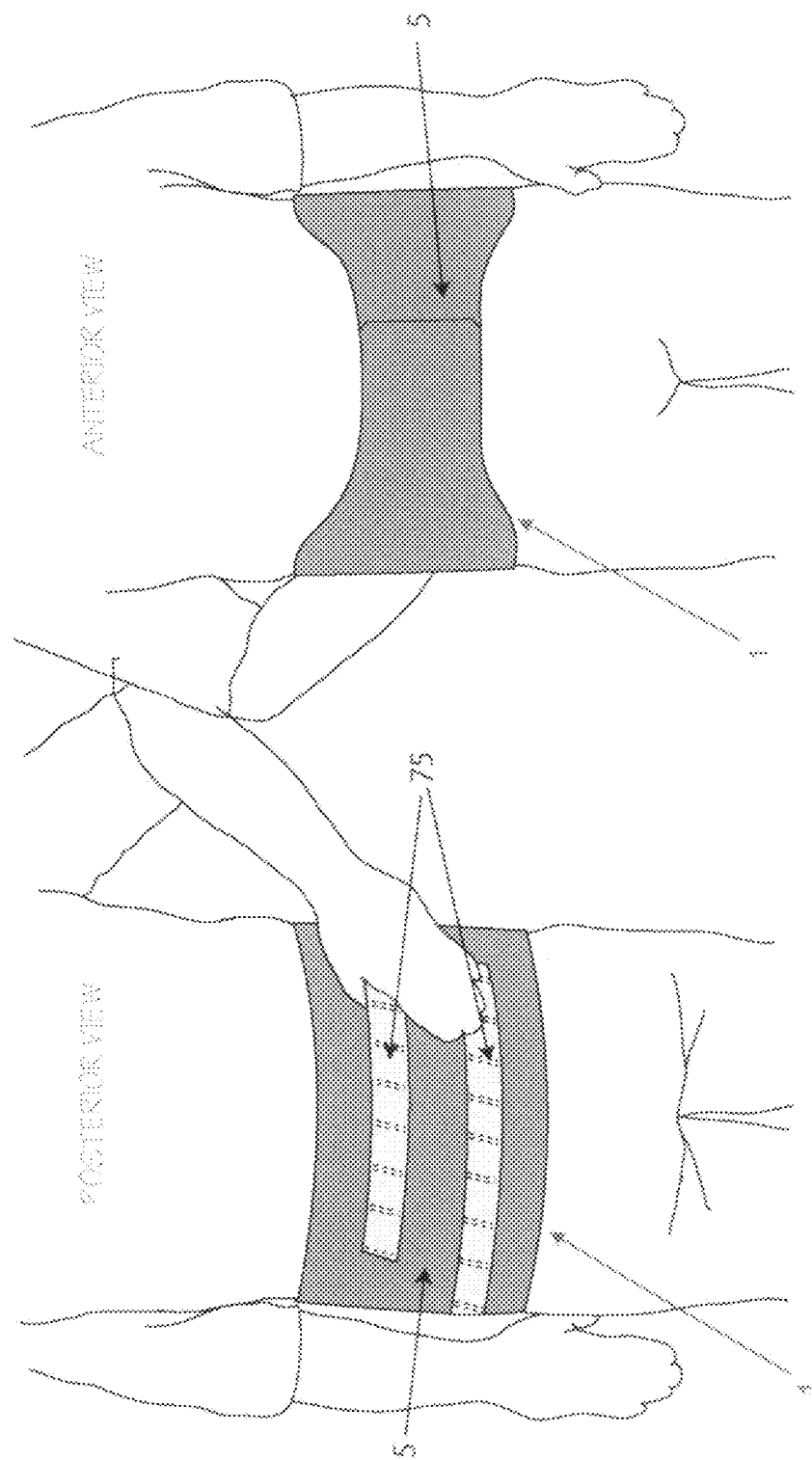

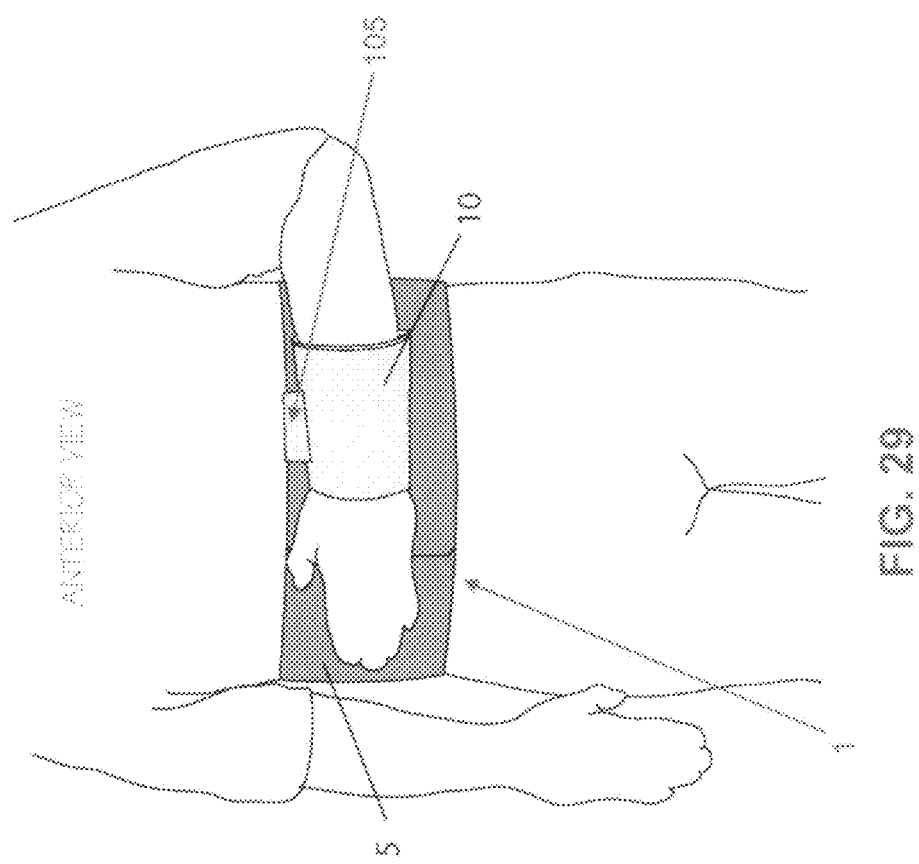

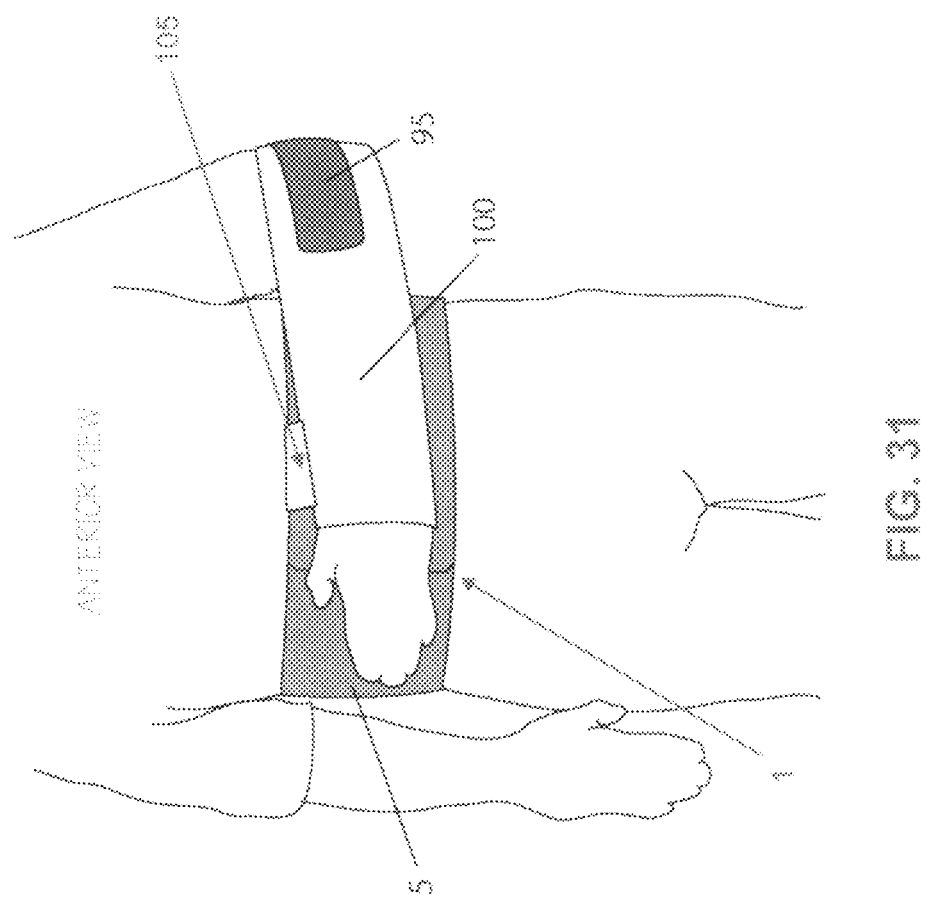
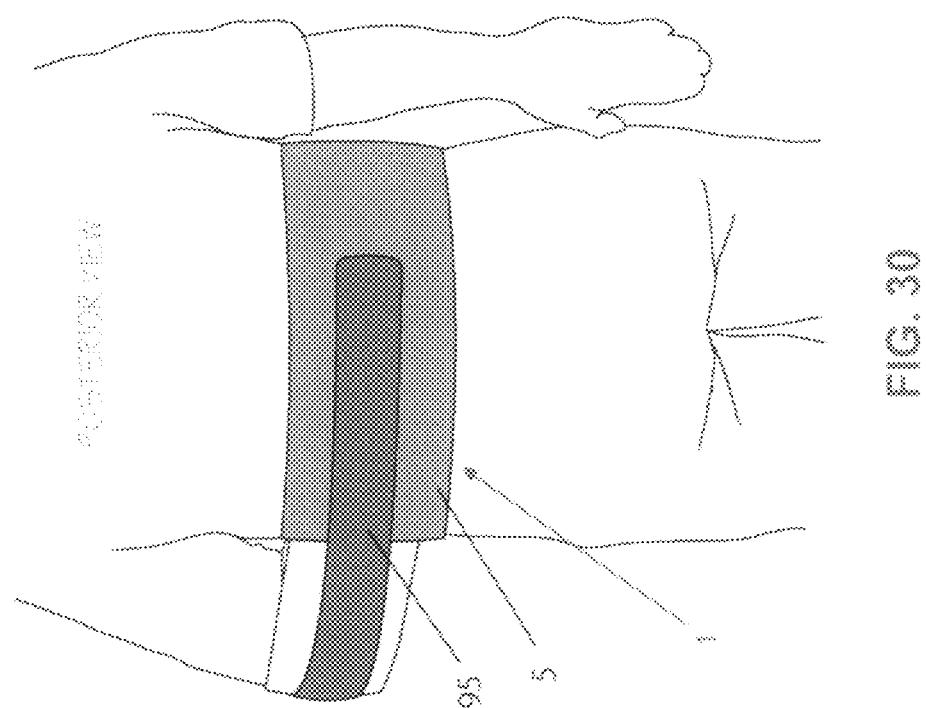

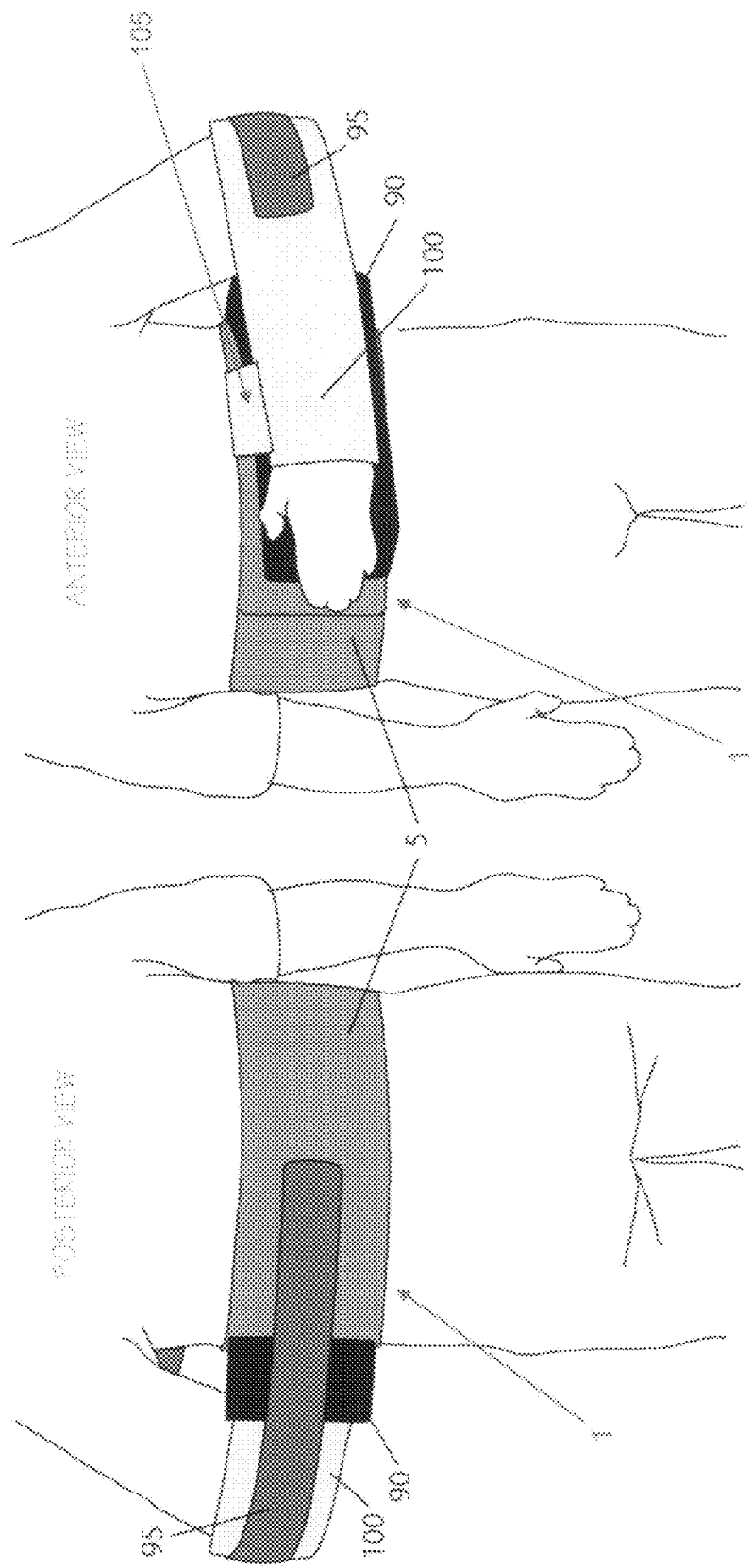

METHOD AND APPARATUS FOR THERAPEUTICALLY SUPPORTING THE ARM OF A PATIENT

REFERENCE TO PENDING PRIOR PATENT APPLICATION

This patent application claims benefit of prior U.S. Provisional Patent Application Ser. No. 61/208,744, filed Feb. 27, 2009 by William S. Barnes et al. for METHOD AND APPARATUS FOR A THERAPEUTIC SLING, which patent application is hereby incorporated herein by reference.

FIELD OF THE INVENTION

This invention relates to physical therapy in general, and more particularly to methods and apparatus for therapeutically supporting the arm of a patient so as to progressively extend the range of motion in a shoulder compromised by a medical pathology and/or by the secondary effects of a surgical intervention.

BACKGROUND OF THE INVENTION

In the treatment of shoulder pathologies such as tendonitis, impingement syndrome, tendonosis, rotator cuff tears, adhesive surgery, etc., post-operative scarring is a common occurrence. Such post-operative scarring can result in a limited range of motion in the shoulder.

More particularly, such post-operative scarring can result in contracture of the joint capsule and the surrounding soft tissue structures, which can itself result in a limited range of motion in the shoulder. In addition, the contracture of the posterior capsule can prevent the rotator cuff from properly stabilizing and depressing the humeral head in abduction. This can, in turn, create a cam effect of the humeral head in abduction, thereby resulting in further limited range of motion, as well as instability of the shoulder. Thus, post-operative scarring is a common source of frustration for patients, since a limited range of motion in the shoulder can lead to a restricted lifestyle.

The current method for restoring a patient's range of motion is through physical therapy, which generally involves joint manipulation, soft tissue stretching and muscle strengthening. However, current methods of soft tissue stretching generally suffer from the fact that, due to the limited time available for a typical therapy session, substantial stretching must be effected at each therapy session. This stretching pushes the limits of the soft tissue, so that the patient frequently experiences significant discomfort during the therapy. Significantly, when the patient experiences this painful traumatic stretching, muscle spasms can occur. These muscle spasms are counterproductive to the stretching process, since they create an antagonistic force which inhibits stretching and thereby undermines the physical therapy. In some cases the pain and muscle spasms experienced by the patient can become so problematic as to require a halt to the normal physical therapy protocol. And in some extreme cases, such pain and muscle spasms may be so severe as to require closed manipulation of the shoulder joint under anesthesia and/or arthroscopic or open capsular releases.

We have determined that, if the soft tissue can be stretched, and then maintained in that stretched condition long enough for any muscle spasms to subside and for muscular relaxation to occur, the soft tissue can then be stretched further in a gentle, relaxed manner so as to facilitate highly effective physical therapy. In other words, we have determined that effective stretching of the capsule can best be achieved by stretching the soft tissue to a first extent, holding the soft tissue in that position for a period of time so that the muscles return to a relaxed state, and then stretching the soft tissue further.

Unfortunately, the methods and apparatus currently used in stretching the soft tissue—either because of the tight time constraints of a typical physical therapy session or because of the inherent mechanics of the apparatus—provide no effective way to stretch the soft tissue, maintain the soft tissue in that stretched condition long enough for muscular relaxation to occur, and then stretch the soft tissue further. Thus, current methods and apparatus do not allow the muscle to relax and cease to be an antagonistic force, which is counterproductive to physical therapy.

Thus, there is an urgent need for an improved method and apparatus which allows the patient's soft tissue to be stretched, held in this stretched condition long enough for muscular relaxation to occur, and then stretched further in a gentle, relaxed manner so as to facilitate effective physical therapy.

SUMMARY OF THE INVENTION

The present invention provides a new method and apparatus for providing physical therapy for restoring a proper range of motion to a joint compromised by a medical pathology and/or by the secondary effects of a surgical intervention.

More particularly, the present invention provides a new method and apparatus for stretching the soft tissue of a joint, maintaining the soft tissue in that stretched condition long enough for muscle relaxation to occur, and then stretching the soft tissue further in a gentle, relaxed manner, so as to facilitate effective physical therapy. More particularly, the present invention comprises the provision and use of a novel therapeutic support that maintains the muscles of the shoulder girdle in a more relaxed state, thereby allowing the patient to more effectively stretch the capsule and other soft tissue structures.

The present invention also provides a new method and apparatus for stretching, and maintaining in that stretched condition, the ligaments of a tightened capsular complex of a shoulder while the shoulder muscles are in a relaxed state so as to avoid muscle spasms and pain, thereby enhancing the healing process.

The present invention may also be used in other types of orthopedic therapy where a patient's range of motion is compromised (e.g., by surgical intervention or pathology) in other planes of motion of the shoulder, or in other joints.

In one preferred from of the present invention, there is provided a method for providing physical therapy to a patient, the method comprising:

providing a therapeutic support comprising a waist belt and a limb support, wherein the limb support is adjustably securable to the waist belt;

positioning the waist belt on the patient and supporting a limb of the patient on the waist belt by attaching the limb of the patient to the limb support and attaching the limb support to the waist belt;

after a suitable period of time, repositioning the limb support on the waist belt so as to stretch the soft tissue of the patient;

after another suitable period of time, repositioning the limb support on the waist belt so as to further stretch the soft tissue of the patient; and repeating the foregoing until the desired physical therapy has been achieved.

In another preferred form of the present invention, there is provided apparatus for providing physical therapy to a patient, the apparatus comprising a therapeutic support comprising a waist belt and a limb support, wherein the limb support is adjustably securable to the waist belt.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 2A, 2B, 2C, 2D and 2E are schematic posterior views showing a preferred manner of using the therapeutic support of the present invention;

FIGS. 3 and 4 are schematic posterior and anterior views, respectively, showing another therapeutic support formed in accordance with the present invention, wherein the therapeutic support includes a higher back and stiffening ribs, and further includes a mitt to hold the patient's hand;

FIGS. 7 and 8 are posterior and anterior views, respectively, showing another therapeutic support formed in accordance with the present invention, wherein the therapeutic support includes additional upper and lower surface areas on the posterior portion of the therapeutic support, and further includes attachment indicators;

FIGS. 9 and 10 are schematic posterior and anterior views, respectively, showing another therapeutic support formed in accordance with the present invention, wherein the therapeutic support includes an extended upper surface area on the posterior portion of the therapeutic support, and further includes a movable patch to which the cuff is selectively attached;

FIGS. 13 and 14 are posterior and anterior views, respectively, showing another therapeutic support formed in accordance with the present invention, wherein the therapeutic support includes a low back extension on the posterior portion of the therapeutic support, a reversible hand mitt including one portion of a hook-and-loop (e.g., Velcro™) material, and a shoulder strap with an extension including another portion of a hook-and-loop (e.g., Velcro™) material;

FIGS. 15 and 16 are posterior and anterior views, respectively, showing another therapeutic support formed in accordance with the present invention, wherein the therapeutic support is formed with a reversible hand mitt for attachment to the posterior portion of the therapeutic support and a handle on the anterior portion of the therapeutic support;

FIGS. 17 and 18 are posterior and anterior views, respectively, of another therapeutic support formed in accordance with the present invention, wherein the therapeutic support includes an expanded lower surface attachment area on the posterior portion of the therapeutic support, and further includes a mechanical attachment system for attaching the cuff to the waist belt;

FIGS. 21 and 22 are posterior and anterior views, respectively, showing another therapeutic support formed in accordance with the present invention, wherein the therapeutic support includes a sliding strap for progressively advancing the position of the cuff along the waist belt, and further includes a ratchet mechanism for controlling the position of the sliding strap;

FIGS. 23 and 24 are posterior and anterior views, respectively, showing another therapeutic support formed in accordance with the present invention, wherein the therapeutic support includes a sliding strap for progressively advancing the position of a hanging cuff along the waist belt, and further includes a push-to-release button for releasing the sliding strap.

FIGS. 25 and 26 are posterior and anterior views, respectively, showing another therapeutic support formed in accordance with the present invention, wherein the therapeutic support includes a waist belt having sewn-in pockets;

FIGS. 27 and 28 are posterior and anterior views, respectively, showing another therapeutic support formed in accordance with the present invention, wherein the therapeutic support includes a waist belt having sewn-in straps to accommodate the thumb, fingers or hand of the patient;

FIG. 29 is an anterior view showing another therapeutic support formed in accordance with the present invention;

FIGS. 30 and 31 are posterior and anterior views, respectively, showing another therapeutic support formed in accordance with the present invention, wherein the therapeutic support includes a shoulder immobilizer accessory;

FIGS. 32 and 33 are posterior and anterior views, respectively, showing another therapeutic support formed in accordance with the present invention, wherein the therapeutic support includes a first abduction accessory.

DETAILED DESCRIPTION OF THE PREFERRED EMBODIMENTS

The present invention provides a new method and apparatus for therapeutically increasing range of motion in a shoulder compromised by a medical pathology and/or by the secondary effects of a surgical intervention. For convenience, the present invention will hereinafter be discussed in the context of its use for post-operative shoulder therapy; however, it should be appreciated that the present invention may also be used for other therapeutic needs of the shoulder and/or for other joints of the body.

Figure 1:
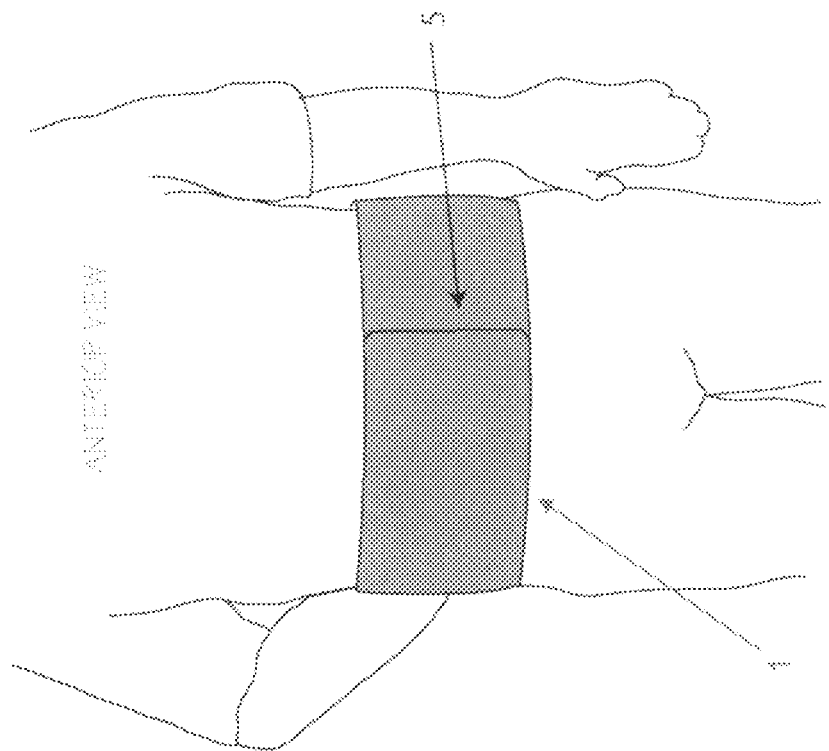
FIGS. 1 and 2 are schematic posterior and anterior views, respectively, showing a therapeutic support constructed and applied in accordance with the present invention, wherein the therapeutic support includes a waist belt and a cuff for supporting the patient's arm.
Figure 2:
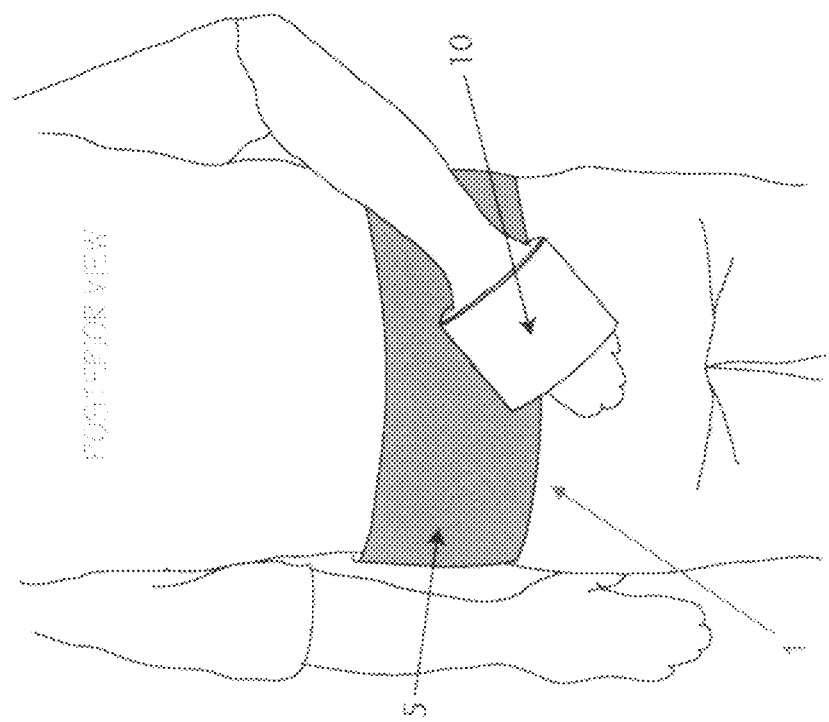

Turning first to FIGS. 1 and 2, there is shown a therapeutic support 1 which comprises a waist belt 5 and a cuff 10. Waist belt 5 is intended to be wrapped around the waist of the patient and fixed in place (preferably on the anterior side of the patient) by a hook-and-loop (e.g., Velcro™) connector or by other means of the sort well known in the art, e.g., snaps, buttons, buckles, etc. Cuff 10 is intended to support the hand/ arm of the patient, and is configured so as to be adjustably attached to waist belt 5. By way of example but not limitation, cuff 10 may be adjustably attached to waist belt 5 by means of a hook-and-loop (e.g., Velcro™) connector or by some other means of the sort well known in the art. It should be appreciated that cuff 10 can be sized and positioned so as to support the patient's hand and/or the patient's hand and wrist/lower arm and/or just the patient's wrist/lower arm, etc.

Looking next at FIGS. 2A, 2B, 2C, 2D and 2E, therapeutic support 1 is preferably used as follows.

First, waist belt 5 is positioned around the waist of the patient, and cuff 10 is placed around the patient's wrist. Then the patient's arm is positioned at their side, with the palm turned outward at hip level. Then cuff 10 is attached to waist belt 5 so as to hold the patient's arm in this position ("Position 1"). Alternatively, if desired, cuff 10 can first be attached to the waist belt, and then the limb of the patient can be attached to cuff 10 (and hence to waist belt 5).

If desired, waist belt 5 may include a belt protrusion 15 (FIG. 2A) which descends below the height of the remainder of waist belt 5. When waist belt 5 is first positioned around the waist of the patient, belt protrusion 15 is turned downward and centered on the hip.

Figures 2A, 2B:
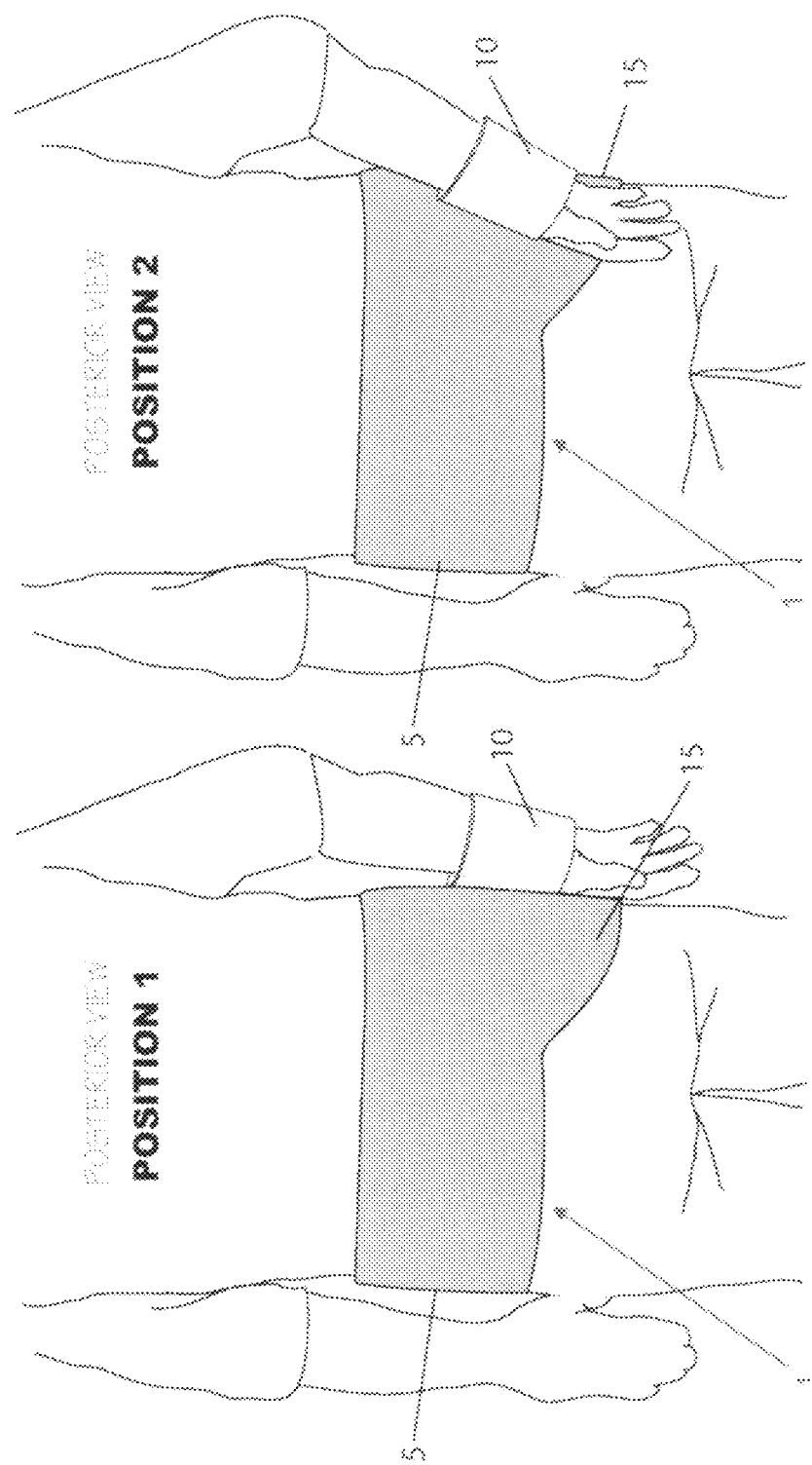

After a period of time has elapsed, and looking now at FIG. 2B, cuff 10 is detached from waist belt 5, the patient's arm is moved slightly around the body toward the posterior side, and then cuff 10 is reattached to waist belt 5 ("Position 2"). In this position, the soft tissue in the patient's shoulder joint will have been stretched slightly, but preferably not so much as to induce pain or muscle spasms.

After a another period of time has elapsed, and in any case long enough for the stretched muscles to relax, cuff 10 is detached from waist belt 5, waist belt 5 is repositioned so that belt protrusion 15 extends upwardly in the middle of the patient's back, the patient's arm is moved further around the body so as to be fully on the posterior side, and then cuff 10 is reattached to waist belt 5, as shown in FIG. 2C ("Position 3"). In this position, the soft tissue in the patient's shoulder joint will have been further stretched slightly, but again preferably not so much as to induce pain or muscle spasms.

After an additional period of time has elapsed, and in any case long enough for the stretched muscles to relax, cuff 10 is detached from waist belt 5, the patient's arm is moved further around the body and up slightly so as to be further extended on the posterior side, and then cuff 10 is reattached to waist belt 5, as shown in FIG. 2D ("Position 4"). In this position, the soft tissue in the patient's shoulder joint will have been still further stretched slightly, but again preferably not so much as to induce pain or muscle spasms.

Finally, after even more time has elapsed, and in any case long enough for the stretched muscles to relax, cuff 10 is detached from waist belt 5, the patient's arm is moved even further around the body and even further upward so as to be further extended on the posterior side, and then cuff 10 is reattached to waist belt 5, preferably on belt protrusion 15, as shown in FIG. 2E ("Position 5"). In this position, the soft tissue in the patient's shoulder joint will have been even further stretched slightly, but again preferably not so much as to induce pain or muscle spasms.

Thus it will be seen that, with the present invention, the patient's shoulder may be progressively stretched, through a series of small but meaningful increments applied over substantial periods of time, so as to slowly stretch the soft tissue of the shoulder, preferably without inducing detrimental pain or muscle spasms. During this time, the patient's limb is supported by therapeutic support 1 so as to keep the limb properly positioned for effective therapeutic stretching. As a result, comfortable and effective therapeutic stretching is substantially continuously applied to the patient's shoulder, whereby to increase the patient's range of motion.

Looking next at FIGS. 3 and 4, there is shown another therapeutic support 1 which is generally similar to the therapeutic support 1 shown in FIGS. 1 and 2. However, in this form of the invention, waist belt 5 includes stiffening ribs 80 in belt protrusion 15. Furthermore, cuff 10 may be replaced with a right-hand mitt 20, which exposes the thumb. Where appropriate, right-hand mitt 20 may be replaced by a left-hand mitt. Mitt 20 may be adjustably attached to waist belt 5 by means of a hook-and-loop (e.g., Velcro™) connector.

Figure 6:
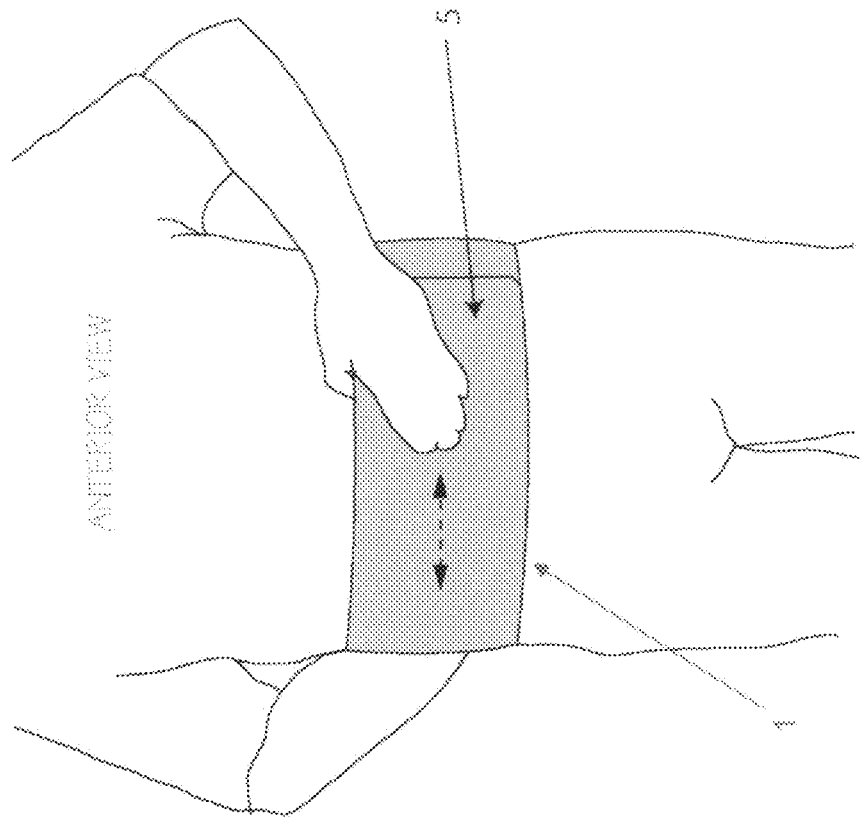
FIGS. 5 and 6 are schematic posterior and anterior views, respectively, showing another therapeutic support formed in accordance with the present invention, wherein the therapeutic support includes an additional lower surface area on the posterior portion of the therapeutic support.
Figure 5:
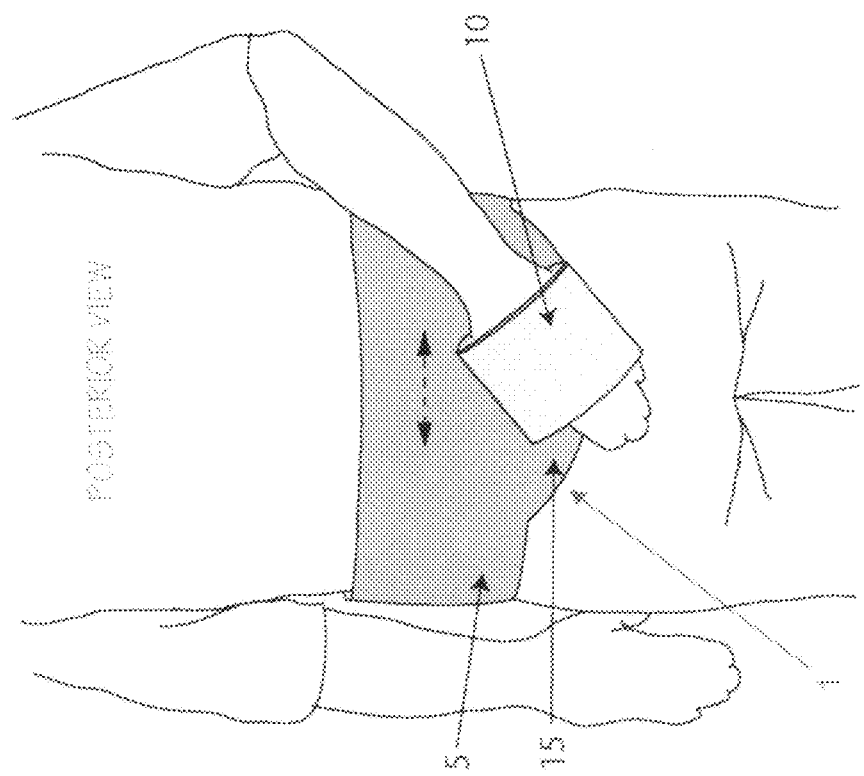

Looking next at FIGS. 5 and 6, there is shown another therapeutic support 1 which is generally similar to the therapeutic support shown in FIGS. 1 and 2. However, in this form of the invention, protrusion 15 is preferably arranged so as to extend downward on the posterior side of the patient, thereby creating an additional surface which can accommodate lower positions for the attachment of cuff 10. Once attached, waist belt 5 may be moved circumferentially around the waist of the patient in order to move cuff 10 laterally during therapy—by way of example but not limitation, this may be done by grasping waist belt 5 on its anterior side and pulling waist belt 5 to the left or right.

Looking next at FIGS. 7 and 8, there is shown another therapeutic support 1 which is generally similar to the therapeutic support shown in FIGS. 1 and 2. However, in this form of the invention, multiple protrusions 15 (preferably extending both upward and downward from the axis of waist belt 5) are provided. If desired, attachment indicators 25 may be printed, embossed, etc. on waist belt 5 (including on the one or more protrusions 15) so as to allow the patient, therapist, or others to properly position cuff 10 relative to waist belt 5, either before or after positioning the waist belt around the waist of the patient. These recommended attachment indicators 25 also provide visual cues for measuring the patient's therapeutic progress.

Looking next at FIGS. 9 and 10, there is shown another therapeutic support 1 which is generally similar to the therapeutic support shown in FIGS. 1 and 2. However, in this form of the invention, waist belt 5 includes a patch 30 for mounting cuff 10 to waist belt 5. Preferably patch 30 is adjustably mounted to waist belt 5 by a hook-and-loop (e.g., Velcro™) connector or by other means of the sort well known in the art so that patch 30 can be positioned on different locations on waist belt 5. Additionally, patch 30 includes a plurality of buttons 35 (or snaps, etc.) which permit cuff 10 to be releasably mounted to different areas of patch 30. Thus it will be seen that with this form of the invention, patch 30 is positioned on a desired location on waist belt 5, and cuff 10 is buttoned, snapped, or otherwise attached to patch 30 so as to allow the cuff to be easily attached and detached from patch 30 and hence to waist belt 5. If desired, cuff 10 may be pivotally connected to patch 30, so as to provide a limited degree of movement to the patient's limb. If desired, waist belt 5 may include belt protrusion 15 which ascends above the height of the remainder of waist belt 5.

Figure 11:
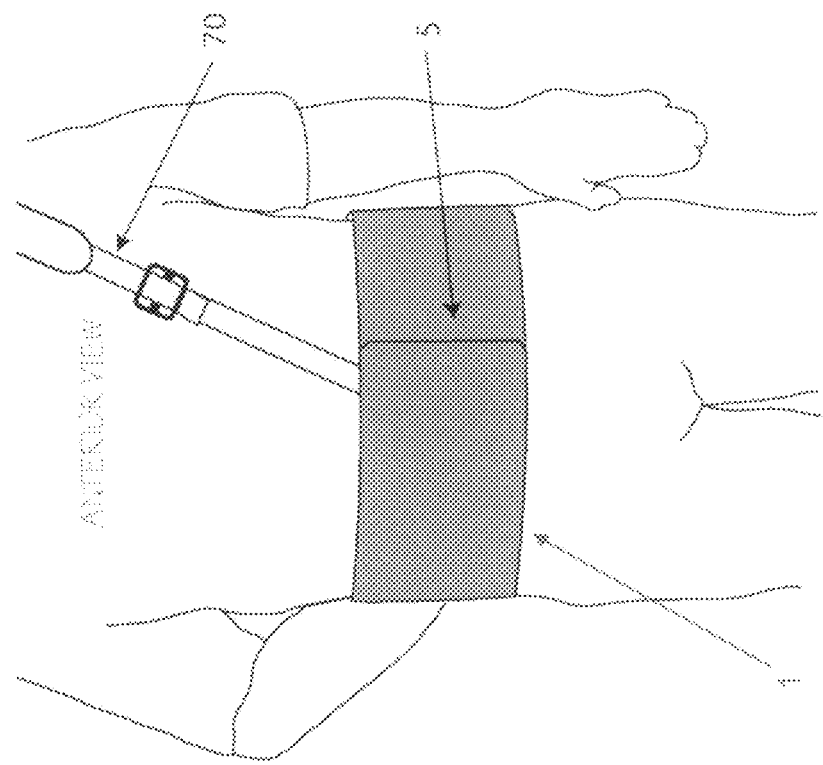
FIGS. 11 and 12 are posterior and anterior views, respectively, showing another therapeutic support formed in accordance with the present invention, wherein the therapeutic support includes a high back on the posterior portion of the therapeutic support, a reversible hand mitt, and a shoulder strap.
Figure 12:
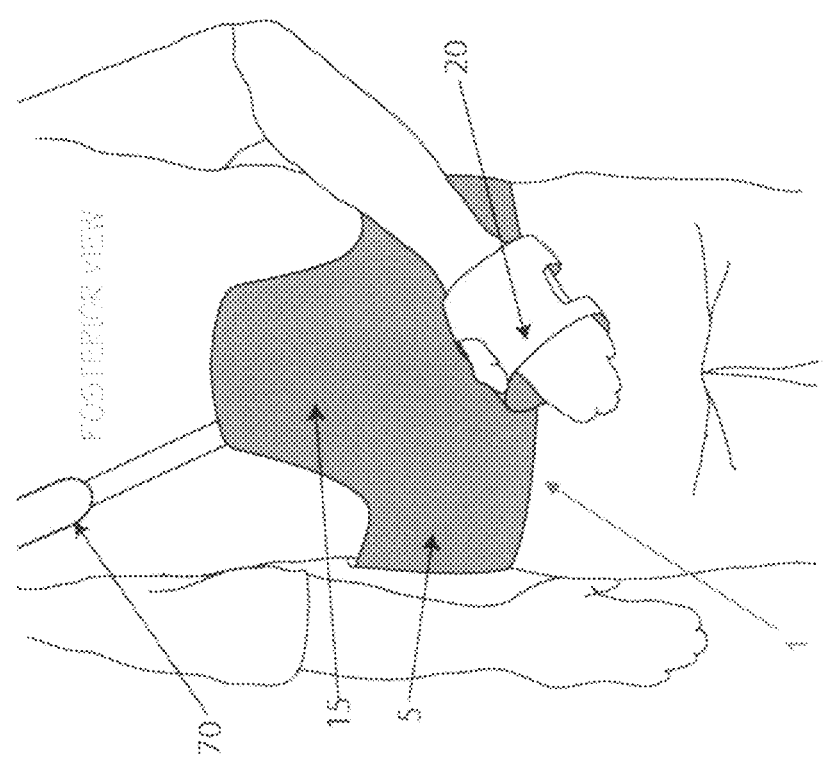

Looking next at FIGS. 11 and 12, there is shown another therapeutic support 1 which is generally similar to the therapeutic support shown in FIGS. 3 and 4. However, in this form of the invention, an adjustable shoulder strap 70 is attached to the therapeutic support, e.g., by a hook-and-loop (e.g., Velcro™) or some other means of the sort well known in the art, and aids in supporting therapeutic support 1 on the waist of the patient. Shoulder strap 70 can be located over the patient's right or left shoulder, i.e., preferably opposite the shoulder to which therapy is being applied.

Looking next at FIGS. 13 and 14 there is shown another therapeutic support 1 which is generally similar to the therapeutic support shown in FIGS. 11 and 12. However, in this form of the invention, a sling extension 85 is included on shoulder strap 70, thereby providing an upper back area on which hand mitt 20 may be attached. If desired, waist belt 5 may include belt protrusion 15 which descends below the height of the remainder of waist belt 5.

Looking next at FIGS. 15 and 16 there is shown another therapeutic support 1 which is generally similar to the therapeutic support shown in FIGS. 5 and 6. However, in this form of the invention, waist belt 5 may omit protrusion 15 and cuff 10 may be replaced by a reversible hand mitt 20. Furthermore, a handle 55 on the anterior side of waist belt 5 provides a pulling means for moving the affected limb further around the body during therapy, i.e., by rotating waist belt 5 circumferentially around the patient's waist.

Looking next at FIGS. 17 and 18, there is shown another therapeutic support 1 which is generally similar to the therapeutic support shown in FIGS. 1 and 2. However, in this form of the invention, snaps 35 are used to releasably secure cuff 10 to waist belt 5. Preferably, a plurality of snaps 35 are provided, so as to permit the location of cuff 10 to be moved during the course of therapy (with or without additional circumferential movement of waist belt 5 about the waist of the patient). Furthermore, snaps 35 preferably provide a pivotal connection between cuff 10 and waist belt 5, so that cuff 10 can rotate with respect to waist belt 5. If desired, waist belt 5 may include belt protrusion 15 which descends below the height of the remainder of waist belt 5.

Figure 20:
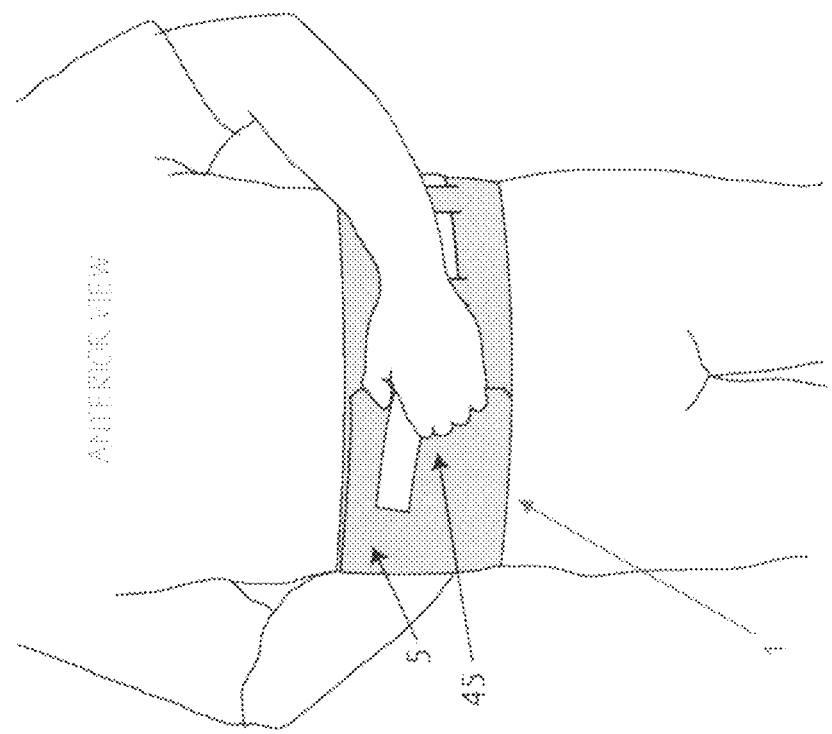
FIGS. 19 and 20 are posterior and anterior views, respectively, showing another therapeutic support formed in accordance with the present invention, wherein the therapeutic support includes a sliding strap for progressively advancing the position of the cuff along the waist belt.
Figure 19:
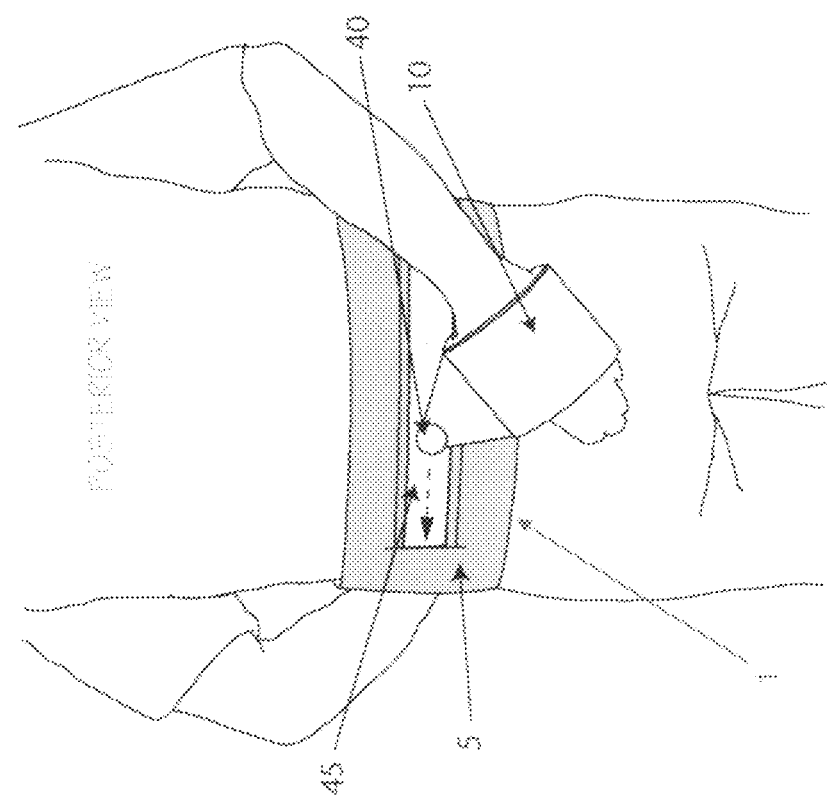

Looking next at FIGS. 19 and 20, there is shown another therapeutic support 1 which is generally similar to the therapeutic support shown in FIGS. 1 and 2. However, in this form of the invention, a movable strap 45 is provided on waist belt 5, and cuff 10 is releaseably secured to movable strap 45 via a grommet or button 40. With this form of the invention, once cuff 10 is attached to movable strap 45 via button 40, movable strap 45 may be pulled on the anterior side of the patient so as move cuff 10 laterally along the waist belt during therapy.

Looking next at FIGS. 21 and 22, there is shown another therapeutic support 1 which is generally similar to the therapeutic support shown in FIGS. 19 and 20. However, in this form of the invention, a ratchet device 50 is provided for selectively tightening movable strap 45.

Looking next at FIGS. 23 and 24, there is shown another therapeutic support 1 which is generally similar to the therapeutic support shown in FIGS. 19 and 20. However, in this form of the invention, a push-to-release button 60 is provided for selectively releasing movable strap 45.

Looking next at FIGS. 25 and 26, there is shown another therapeutic support 1 which generally comprises a waist belt 5 which includes at least one pocket 65. Again, waist belt 5 is intended to be wrapped around the waist of the patient and secured in place (preferably on the anterior side of the patient) by a hook-and-loop (e.g., Velcro™) connector or by other means of the sort well known in the art, e.g., snaps, buttons, buckles, etc. The at least one pocket 65 is intended to support the hand/arm of the patient. The at least one pocket 65 may be sewn-in, in which case a plurality of pockets are preferably provided, in order to allow progressive stretching of the soft tissue; alternatively, just one pocket 65 may be provided, in which case stretching is achieved by periodically circumferentially turning waist belt 5. In another form of the invention, the at least one pocket 65 may be repositionable on waist belt 5, such as with a hook-and-loop (e.g., Velcro™) connector, in order to allow progressive stretching of the patient's soft tissue.

Looking next at FIGS. 27 and 28, there is shown another therapeutic support 1 which is generally similar to the therapeutic support shown in FIGS. 25 and 26, except that the at least one pocket 65 is replaced by sewn-in strips 75 on the posterior side of waist belt 5. Sewn-in strips 75 preferably each include a plurality of chambers along their length which will accept and support the thumb, fingers or hand of the affected arm, in order to allow progressive stretching of the patient's soft tissue. Waist belt 5 is reversible by turning waist belt 5 upside down.

Looking next at FIG. 29, there is shown another therapeutic support 1 which is generally similar to the therapeutic support shown in FIGS. 1 and 2, except that cuff 10 may be mounted to waist belt 5 via a hook 105. As seen in FIG. 29, cuff 10 may be mounted to the anterior side of waist belt 5.

Looking next at FIGS. 30 and 31, there is shown another therapeutic support 1 which is generally similar to the therapeutic support shown in FIG. 29, except that cuff 10 may be replaced by a sleeve 100 which is long enough to cover substantially the entire forearm of the patient, and an immobilizer strap 95 may be provided to stabilize sleeve 100 relative to the waist belt 5. In one preferred form of the invention, immobilizer strap 95 extends circumferentially around the patient.

Looking next at FIGS. 32 and 33, there is shown another therapeutic support 1 which is generally similar to the therapeutic support shown in FIGS. 30 and 31, except that an abduction pillow 90 is provided between sleeve 100 and waist belt 5.

Figure 35:
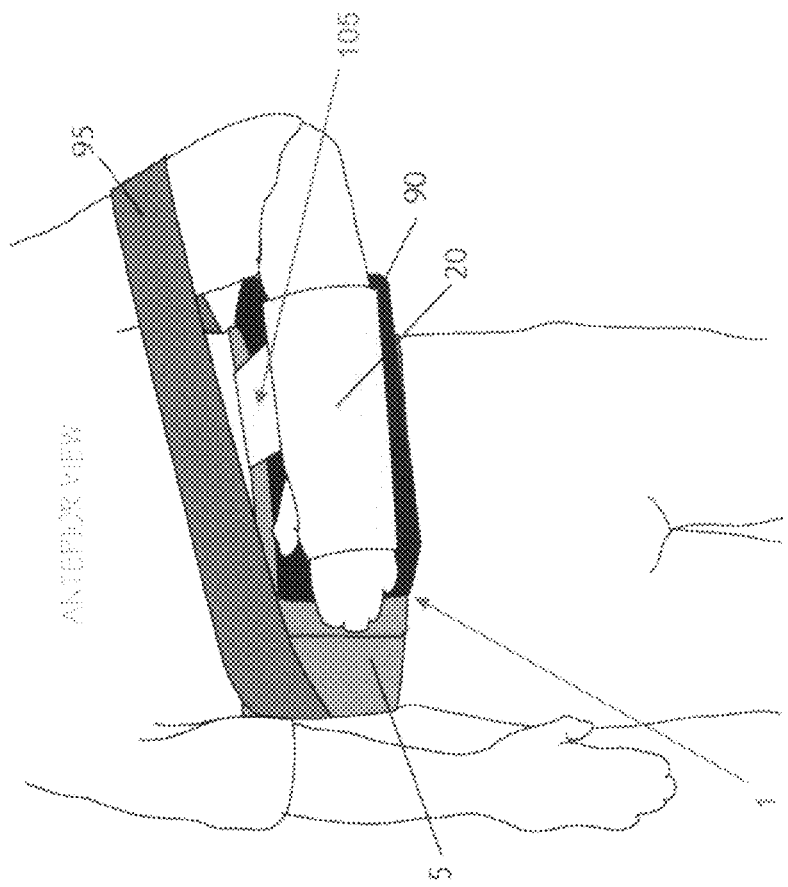
FIGS. 34 and 35 are posterior and anterior views, respectively, showing another therapeutic support formed in accordance with the present invention, wherein the therapeutic support includes a third abduction accessory.
Figure 34:
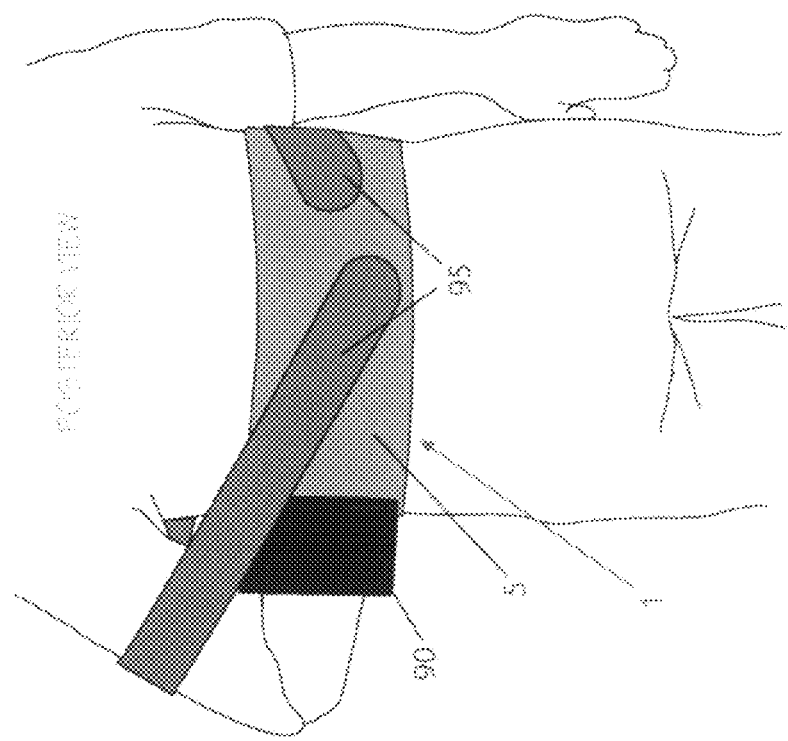

Looking next at FIGS. 34 and 35, there is shown another therapeutic support 1 which is generally similar to the therapeutic support shown in FIGS. 32 and 33, except that an immobilizer strap 95 is provided to stabilize the upper arm of the patient. Preferably immobilizer strap 95 comprises two ends, with each end being releasably secured to the posterior side of waist belt 5.

Some Aspects of the Invention

The therapeutic support comprises (i) a waist belt, and (ii) a cuff, hand mitt, pocket or other structure configured to hold and support the hand and/or wrist/lower arm of the patient and may be repositioned as required.

The waist belt and cuff, hand mitt, pocket or other structure may be produced from various fabrics, or a combination of other materials (e.g., plastic, Velcro™, elastic, etc.).

The therapeutic support may incorporate a shoulder strap to further support the waist belt.

The therapeutic support may be constructed so as to be reversible, or it may be constructed in a left-only or right-only configuration.

The therapeutic support may be sized to fit all (or most) people, or it may come in specific sizes.

The therapeutic support's waist belt may incorporate an extension device to accommodate large (e.g., obese) patients.

The therapeutic support may incorporate fixed (non-movable) hand supports or cuffs.

The therapeutic support may incorporate rotating/freely swinging hand supports or cuffs.

A Preferred Method of Use

1. The therapeutic support's waist belt is wrapped around the patient's body at the waist level.
2. The therapeutic support's cuff is affixed to the waist belt.
3. The patient inserts his/her hand into the cuff, relaxes the affected arm and wears the device for a prescribed period of time, and in any case long enough for the muscles of the shoulder to relax.

4. The patient, therapist or other person moves the cuff further around body to stretch the soft tissue and thereby intensify therapy.

5. After a suitable period of time has passed, and in any case long enough for the muscles of the shoulder to relax, the cuff is detached from the waist belt and repositioned so as to further stretch the soft tissue of the patient.

6. The foregoing process is continued, with the cuff periodically being moved along the waist belt so as to stretch the soft tissue of the patient, retained in that position for a suitable period of time, and in any case long enough for the muscles of the shoulder to relax, and then moved again, until the desired therapeutic results have been achieved.

Some Advantages/Benefits of the Present Invention

The therapeutic support allows for excellent rehabilitation of the ligamental capsule complex of the shoulder, promoting outstanding long-term comfort, improved range of motion and increased physical ability, resulting in excellent patient outcomes.

Modifications

It will be understood that many additional changes in the details, materials, steps and arrangements of parts, which have been herein described and illustrated in order to explain the nature of the invention, may be made by those skilled in the art while remaining within the principles and scope of the present invention.

What is claimed is:

1. A method for providing physical therapy to a patient, the method comprising:
   providing a therapeutic support comprising a waist belt and a limb support, wherein the limb support is adjustably securable to the waist belt;
   positioning the waist belt on the patient and supporting a limb of the patient on the waist belt by attaching the limb of the patient to the limb support and attaching the limb support to the waist belt;
   after a suitable period of time, repositioning the limb support on the waist belt so as to stretch the soft tissue of the patient;
   after another suitable period of time, repositioning the limb support on the waist belt so as to further stretch the soft tissue of the patient; and
   repeating the foregoing until the desired physical therapy has been achieved.

2. A method according to claim 1 wherein the desired physical therapy comprises extending the range of motion of a shoulder.

3. A method according to claim 1 wherein the waist belt comprises an elongated length having first and second ends, and further comprising a connector for securing the first end of the waist belt to the second end of the waist belt.

4. A method according to claim 3 wherein the connector comprises a hook-and-fastener connector.

5. A method according to claim 1 wherein the waist belt comprises a protrusion extending upwardly or downwardly from the plane of the waist belt.

6. A method according to claim 1 wherein the waist belt comprises a first protrusion extending upwardly from the plane of the waist belt, and a second protrusion extending downwardly from the plane of the waist belt.

7. A method according to claim 1 wherein the waist belt comprises stiffening ribs.

8. A method according to claim 1 wherein the limb support comprises one from the group consisting of a cuff, a mitt, a sleeve, a pocket, and a member providing openings for receiving one or more of the digits of the limb.

9. A method according to claim 1 wherein the limb support is adjustably secured to the waist belt by one from the group consisting of a hook-and-fastener connector, a button, a snap and a hook.

10. A method according to claim 1 wherein the limb support is adjustably secured to the waist belt by an intermediate member.

11. A method according to claim 10 wherein the intermediate member comprises one from the group consisting of a patch and a movable strap.

12. A method according to claim 10 wherein the intermediate member comprises a movable strap, and further wherein the movable strap is connected to the waist belt by one from the group consisting of a ratchet device and a push-to-release button.

13. A method according to claim 1 wherein the therapeutic support further comprises a shoulder strap.

14. A method according to claim 1 wherein the period of time is at least as long as it takes for the muscles of the shoulder to relax.

15. A method according to claim 1 wherein the therapeutic support further comprises an abduction pillow.

16. A method according to claim 1 wherein the therapeutic support further comprises an immobilizer strap.

17. Apparatus for providing physical therapy to a patient, the apparatus comprising a therapeutic support comprising a waist belt and a limb support, wherein the limb support is adjustably securable directly to the waist belt on the lateral or posterior side of the patient's body, additionally, the limb support is adjustably secured on the lateral or posterior side of the patient's body to the waist belt by an intermediate sliding member, comprising 1) a sliding strap circumferential and coplanar to the belt and partially encapsulated within the belt and 2) an attachment device securing the limb support to the sliding member.

* * * * *